United States Patent
Pan

(10) Patent No.: US 6,192,523 B1
(45) Date of Patent: Feb. 27, 2001

(54) DIVING MASK

(75) Inventor: Chen-Lieh Pan, Ilan Hsing (TW)

(73) Assignee: QDS Injection Molding Inc., San Diego, CA (US)

( * ) Notice: Subject to any disclaimer, the term of this patent is extended or adjusted under 35 U.S.C. 154(b) by 0 days.

(21) Appl. No.: 09/484,246

(22) Filed: Jan. 18, 2000

(51) Int. Cl.[7] .................................................. A61F 9/02
(52) U.S. Cl. ................................................ 2/428; 2/441
(58) Field of Search .............................. 2/428, 430, 440, 2/441, 442, 443, 431, 432, 439

(56) References Cited

U.S. PATENT DOCUMENTS

| | | | |
|---|---|---|---|
| 2,706,815 | * | 4/1955 | Parmelee ................................. 2/441 |
| 2,846,684 | * | 8/1958 | Hill ......................................... 2/441 |
| 3,505,680 | * | 4/1970 | Ring ..................................... 2/441 X |
| 5,564,132 | * | 10/1996 | Kuo ..................................... 2/441 X |
| 5,682,621 | * | 11/1997 | Park ......................................... 2/441 |

* cited by examiner

*Primary Examiner*—Peter Nerbun
(74) *Attorney, Agent, or Firm*—Dougherty & Troxell

(57) ABSTRACT

A structural improvement of a diving mask which consists of a main frame, a sub-frame, a lens and a skirt. Tenons are provided on the sub-frame, engaging mortises on the lens. A soft connecting edge is provided on the skirt, which is closely connected with a periphery of the lens. A rigid structure is established by the tenon jointing the sub-frame with the lens, and the connecting frame of the skirt is closely connected with periphery of the lens, when the main frame is connected with sub-frame. This construction allows the diving mask lens removal and keeps a stable connecting state after its assembly.

1 Claim, 3 Drawing Sheets

DIVING MASK

FIELD OF THE INVENTION

The present invention relates to structural improvement of a diving mask, especially, to structural improvement of the assembly between the lens and the main frame, or sub-frame for a diving mask.

BACKGROUND OF THE INVENTION

The conventional manufacturing method of a diving mask, which is connecting the lens with materials such as plastics (silicone etc.) when in moulding, then connect to a main frame and skirt (as shown in FIG. 1), has at least the following disadvantages:

1. The lens is damageable when removing or exchanging the lens having for different sighted degrees (such as nearsighted, farsighted, presbyopic . . . ) or because it is difficult to reassemble, as a result a leaking phenomenon occurs at the edge of the lens.

2. The plastic is closely connected with the lens because the lens (or glass) is directly placed into the die cavity during injection. The thickness of glass due to tolerance is not easily controlled in a certain range, and because there are some problems relating to heat-expanding and cold-contracting during injection, which causes undesired breaking and a latent danger for the eyes of a user.

SUMMARY OF THE INVENTION

The object of the present invention is to provide a structure of a diving mask consisting of a main frame, a sub-frame, a lens and a skirt which can be removed or assembled in order to exchange the lens or process the lens, which has still a stable structure after assembly and does not cause damage of leakage.

The technical solution embodying the above-mentioned object of the present invention is as below. The structural improvement of the diving mask which consists of a main frame, a sub-frame, a lens and a skirt, wherein there are fitting slots provided on the main frame and protrusions on the sub-frame. Tenons are provided on the sub-frame and mortises on the lens, and a soft connecting edge is provided on the skirt which can be closely connected with the periphery of lens. A rigid structure is established by means of the tenon jointing the sub-frame with the lens, the connecting frame of the skirt is closely connected with the periphery of the lens when the main frame is connected with the sub-frame. The above-mentioned construction allows the diving mask removal and keeps still a stable connecting state after its assembly. The mortises on the lens and the tenons on the sub-frame can be connected to each other, the quantity and positions of mortises provided on the lens and tenons provided on the sub-frame can be 1~10 groups.

DETAILED DESCRIPTION OF THE PREFERRED EMBODIMENT

Figure 1:
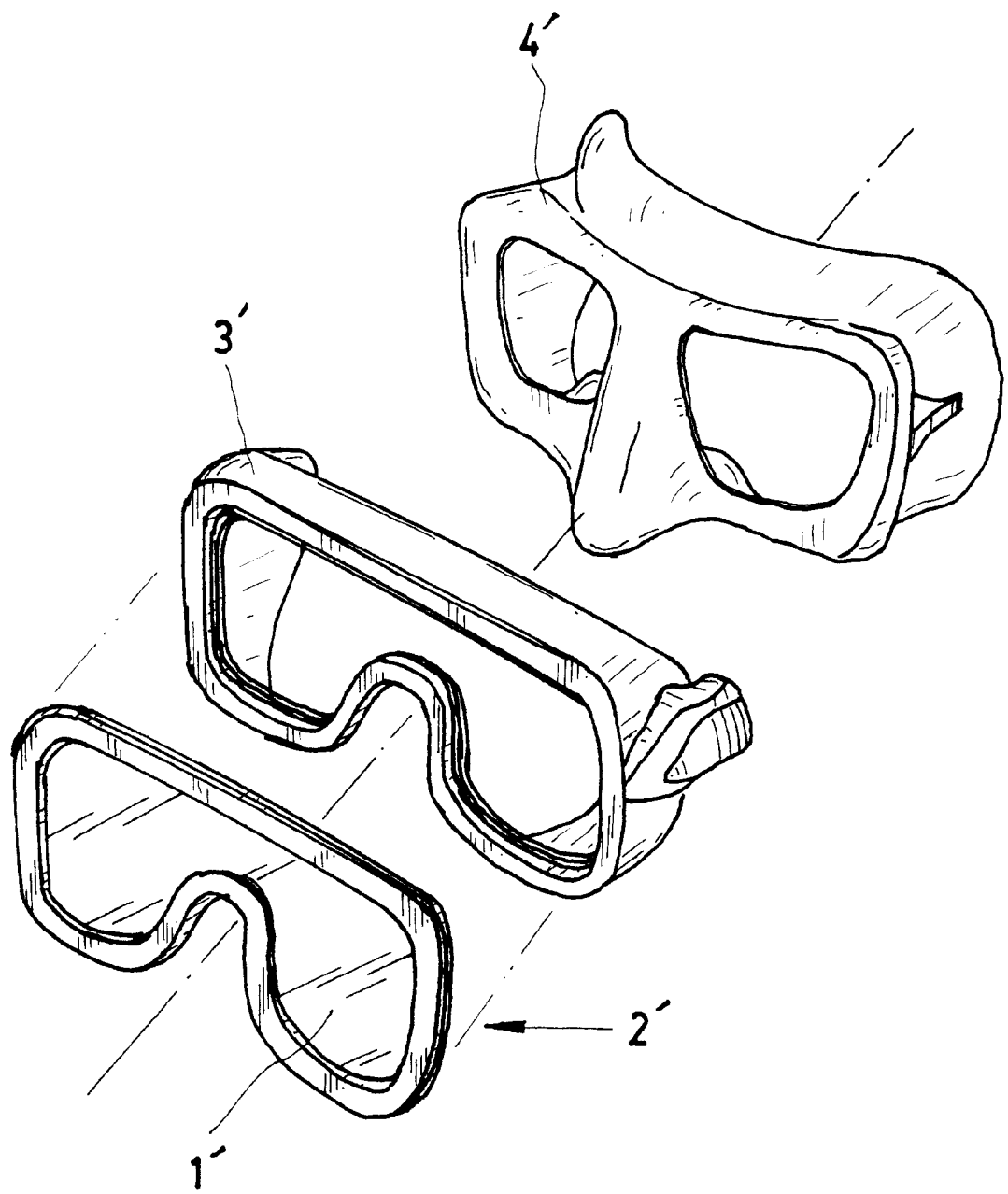
FIG. 1 is an exploded view of a conventional diving mask.

An exploded view for the structure of a conventional diving mask is shown in FIG. 1, wherein the periphery of lens 1' forms sub-frame 2' by fixing a plastic water-proof layer, and then is connected with main frame 3' and skirt 4'.

Figure 2:
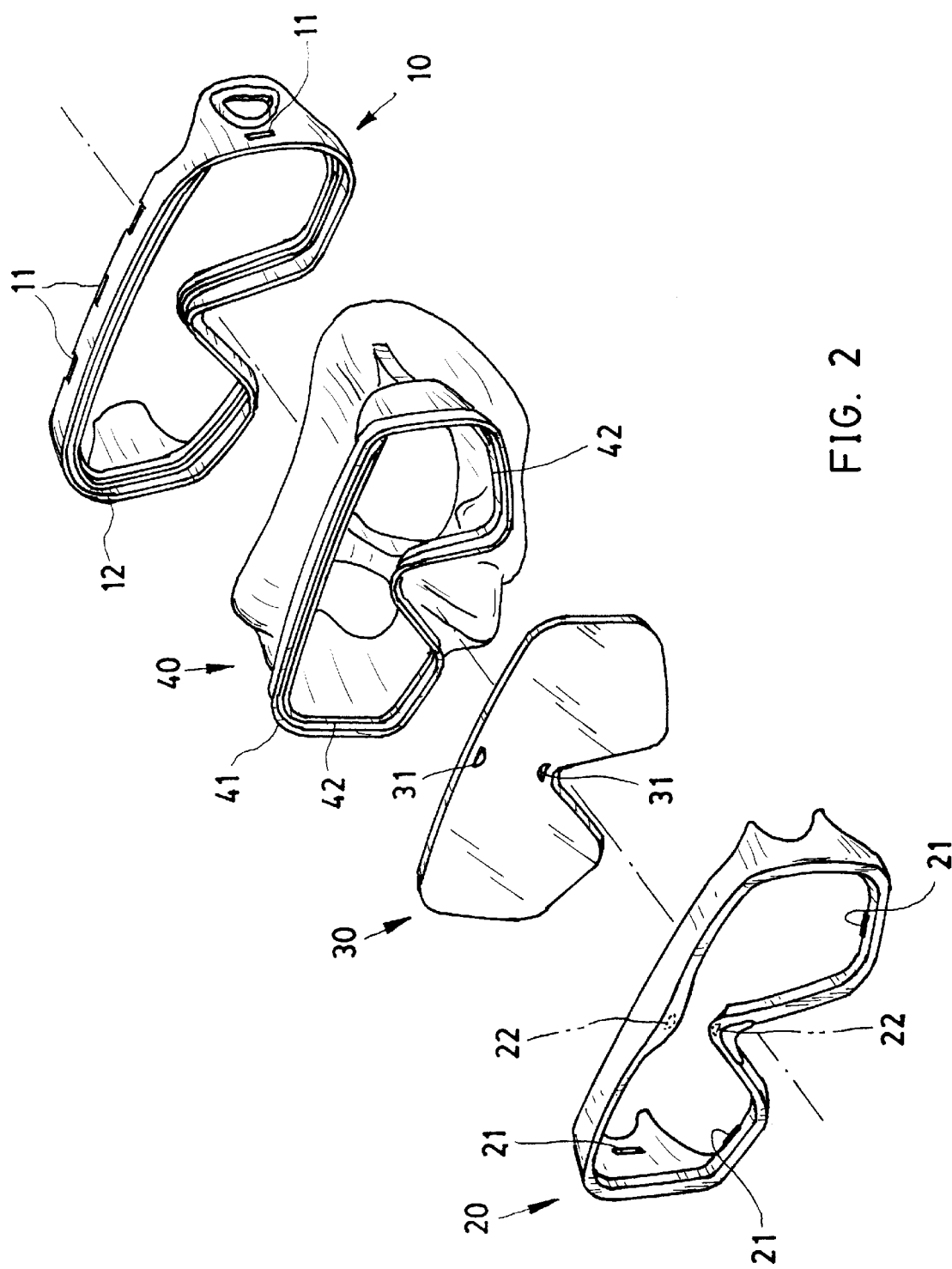
FIG. 2 is an exploded view of the present invention.
Figure 3:
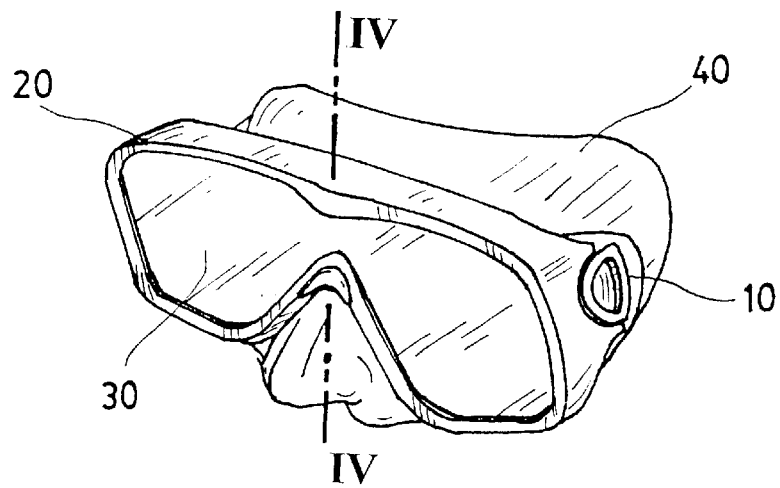
FIG. 3 is a perspective view of the present invention.
Figure 4:
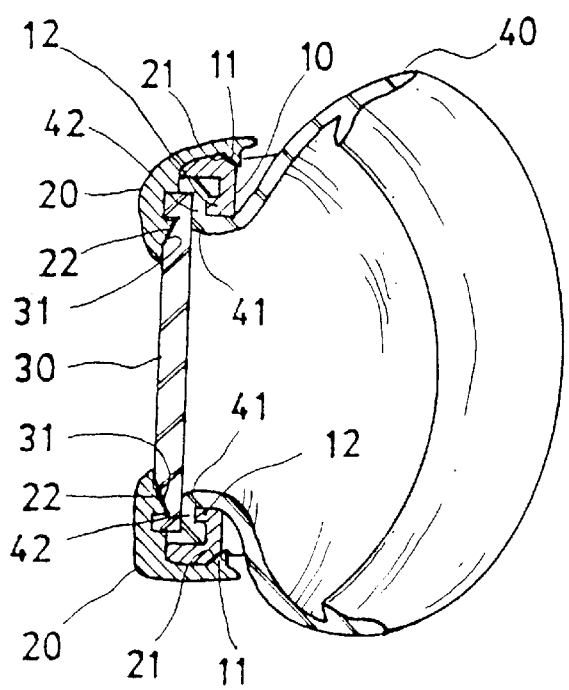
FIG. 4 is a longitudinal sectional view taken along the sectional line IV—IV of FIG. 3.

The structure of the present invention is as shown in FIGS. 2, 3, 4, its construction includes mainly a main frame 10, a sub-frame 20, a lens 30 and a skirt 40.

The main frame 10 and sub-frame 20 are connected by way of fitting slots 11 and protrusions 21 engaging each other. The lens 30 is placed into sub-frame 20, the main frame 10 and skirt 40 can be integrated by means of connecting main frame 10 and sub-frame 20.

There are tenons 22 provided on the sub-frame 20, which are fitted with mortises 31 provided on the lens 30. The position and quantity of tenons 22 and mortises 31 which are fitted each other, may be varied according to the practical needs and configurations of the frame. One group to ten groups can be provided, in order to establish rigid connection between the elements, that is not easily deformed between sub-frame 20 and lens 30 due to external forces, and cause relative displacement or separation thereof.

The skirt 40 is conventional, and is made of rubbery materials (or soft silicone). The frame edge 41 of skirt 40 can be connected with frame body 12 of main frame 10 by a mode of deformation (ref. to FIG. 4).

The contacting position of skirt 40 and lens 30 is the connecting frame 42 in which the lens 30 can be placed in a close fitting state.

The tenons 22 are connected with mortises 31, when the main frame 10 and skirt 40 are connected, the lens 30 is placed into connecting frame 42, and the main frame 10 with sub-frame 20 are pressed by means of slot 11 and protrusion 1, forming a connected state. At this time, the sub-frame 20 can make only a relatively sight deformation because the sub-frame 20 with the lens 30 are in a rigid connected state due to connecting tenons 22 and mortises 31.

The joint of the connecting frame 42 with lens 30 is subjected to the pressure between main frame 10 and sub-frame 20, which forms a close fitting state between the connecting frame 42 and lens 30. Water cannot enter into the inside of skirt 40 through the gap between both elements under this state.

In summary, after assembling the elements of the present invention, it has a structural state which is not deformable and is leakless. In addition, the structure of the present invention can be disassembled by separating the protrusions 21 and slots 11 in order to process or exchange lens 30, and such elements can be easily reassembled.

The present invention forms a rigid connection between sub-frame 20 and lens 30. The foregoing description is provided for illustrative purposes only. The scope of the present invention is defined solely by the appended claims.

What is claimed is:

1. A diving mask having a watertight construction with a removable lens and comprising:

a) a main frame having a frame body with an open center portion and a plurality of spaced apart fitting slots formed in an outer periphery of the frame body;

b) a flexible skirt having a rear portion configured to engage a face of a user around the user's eyes and a front portion with a connecting frame engaging an inner portion of the frame body;

c) a lens having a rear surface and a front surface with a plurality of mortises adjacent to an edge portion thereof; and, d) a sub-frame having an opening, a first portion with a plurality of tenons engaging the plurality of mortises in the lens to removably mount the lens in the sub-frame, and a second portion, spaced from the first portion, having a plurality of sub-frame, and a second portion, spaced from the first portion, having a plurality of protrusions removably engaging the plurality of fitting slots so as to removably attach the sub-frame to the frame body whereby the rear surface of the lens tightly contacts the front portion of the flexible skirt.

* * * * *